(12) United States Patent
Fei et al.

(10) Patent No.: US 11,559,598 B2
(45) Date of Patent: Jan. 24, 2023

(54) ALCOHOL FREE, LOW VISCOSITY, AND HIGH WATER CONTENT AIR FRESHENER COMPOSITIONS

(71) Applicant: Belle-Aire Fragrances, LLC, Mundelein, IL (US)

(72) Inventors: Xiang Fei, Buffalo Grove, IL (US); Jeremy David, Chicago, IL (US); Jerome Bellak, Hawthorne Woods, IL (US); Donald Conover, Jr., Grayslake, IL (US)

(73) Assignee: Belle-Aire Fragrances, LLC, Mundelein, IL (US)

( * ) Notice: Subject to any disclaimer, the term of this patent is extended or adjusted under 35 U.S.C. 154(b) by 222 days.

(21) Appl. No.: 17/085,678

(22) Filed: Oct. 30, 2020

(65) Prior Publication Data
US 2022/0133934 A1 May 5, 2022

(51) Int. Cl.
*A61L 9/01* (2006.01)
*A61L 9/013* (2006.01)

(52) U.S. Cl.
CPC ............. *A61L 9/01* (2013.01); *A61L 9/013* (2013.01)

(58) Field of Classification Search
CPC ............. A61L 9/01; A61L 9/013; C11D 1/00; C11D 7/263; C11D 7/266; C11D 7/40
See application file for complete search history.

(56) References Cited

U.S. PATENT DOCUMENTS

| 4,842,766 | A  | * | 6/1989 | Blehm ............... | A61K 8/062 987/110 |
| 5,415,813 | A  | * | 5/1995 | Misselyn ............ | C11D 3/50 510/423 |
| 6,454,876 | B1 | * | 9/2002 | Ochomogo .......... | C11D 3/201 510/276 |
| 2008/0023569 | A1 | * | 1/2008 | O'Leary ............. | A61L 9/01 239/44 |
| 2008/0056959 | A1 | * | 3/2008 | Cuthbert ............. | A61L 9/145 422/123 |
| 2012/0097754 | A1 | * | 4/2012 | Vlad .................. | A61L 9/01 512/26 |

OTHER PUBLICATIONS

Xu, Jie, Song, Jiaxin, Deng, Huanhuan and Hou, Wanguo, "Surfactant-free microemulsions of 1-butyl-3-methylimidazolium hexafluorophosphate, diethylammonium formate, and water" (Langmuir, downloaded from http://pubs.acs.org), ACS Publications, Jun. 11, 2018 (30 pages).

Xu, Jie, Yin, Aolin, Zhao, Jikuan, Li, Dongxiang and Hou Wanguo, "Surfactant-Free Microemulsion Composed of Oleic Acid, n-Propanol, and H2O", The Journal of Physical Chemistry B 2013, 117, 450-456, ACS Publications, Dec. 11, 2012 (7 pages).

* cited by examiner

*Primary Examiner* — Pamela H Weiss
(74) *Attorney, Agent, or Firm* — Clark Hill PLC

(57) ABSTRACT

An alcohol free, low viscosity, and high-water content air freshener composition is provided. The transparent microemulsion system is stable at a broad range of temperatures. The main ingredient of the composition is water. The composition is free of conventionally-used amphiphilic surfactants including ionic and non-ionic surfactants. The composition contains an oil phase, an aqueous phase and at least one glycol ether solvent. The system is compatible for a wide scope of water-immiscible ingredients that are used in fragrances and flavors.

16 Claims, 2 Drawing Sheets

ALCOHOL FREE, LOW VISCOSITY, AND HIGH WATER CONTENT AIR FRESHENER COMPOSITIONS

RELATED APPLICATIONS

None.

BACKGROUND OF THE INVENTION

Air care products are increasingly used to scent the ambient air in places like private homes, commercial buildings and public areas. These products take many different formats including candles, wax melts, gels, pump sprays, aerosol sprays, reed diffusers, piezo diffusers, plug-ins, and so on.

Water is often used as the major ingredient in many of these products such as gel cones, pump sprays and scented water beads. However, because most fragrance oils have limited water solubility, a component known as a "solubilizer" allows the dispersal of water-immiscible fragrance oils into the water such that the composition is clear or nearly clear. Ethanol or isopropyl alcohol has often been used to solubilize various levels (1-20%) of oils for different perfume types such as Eau de Toilette (EDT) and Eau de Parfum (EDP). However, because the ethanol content is typically over 50%, such products have a low flash point. In addition to being flammable, these compositions have a high Volatile Organic Compound (VOC) content, prohibiting their uses in certain categories of air care products.

Amphiphilic surfactants are used to decrease the surface tension between oil phase and water phase. Use of such surfactants can lower or eliminate the use of ethanol or other short chain alcohols and create the clear aqueous compositions. When appropriate surfactants are applied, fragrance oils can form oil-in-water (o/w) or bicontinuous microemulsions in water. There have been extensive studies on formation and properties of microemulsions, for example, the ones reviewed in "Nanoemulsions versus Microemulsions: Terminology, Differences, and Similarities" by McClements. Soft Matter, 2012, 8, 1719-1729, incorporated herein by reference. Microemulsions are thermodynamically stable and optically clear. They require low energy to prepare, and sometimes, the formation is spontaneous and instant. The colloidal microstructures typically have a size in the range of 10-100 nm which is less than 25% of the wavelength of visible light. That makes them unable to scatter any visible light, rendering them the crystal-clear appearance. Further, glycol ethers are sometimes used in conjunction with amphiphilic surfactants as co-solvents or solubilizing aids, for example as disclosed in U.S. Pat. No. 9,511,165 and "Properties and Applications of Microemulsions" by Klier et al., Advanced Materials, 2000, 12, 1751-1757, incorporated herein by reference.

However, there are quite a few disadvantages using these amphiphilic surfactants. For instance, for air fresheners that use wicks such as reed diffuser and plug-ins, both non-ionic and ionic surfactants clog the wicks and slow the diffusion through wicks, thereby impeding the performance. Indeed, this is a major reason why these air fresheners use organic solvent-based formulas. Further, high amounts of surfactants will often increase the viscosity of the products. Typically, to solubilize one part of a lipophilic fragrance oil, between 2 and 9 parts of surfactants need to be used, depending on the lipophilicity and water solubility of the ingredients. Thus, the product viscosity can increase significantly when incorporating a high level of lipophilic fragrance such as citrus oils. This will prevent the proper use of some formats such as pump spray and aerosol spray which requires the liquid to be thin. Further, foaming is a common character of surfactants. High amounts of surfactants can trap air inside the formula for a long period of time. This presents a potential challenge for both the usage and manufacturing process of some products. For example, aerosol sprays require the formulas to foam minimally for a smooth application. In addition, the manufacturing of water-based air freshener gels needs to remove all the air bubbles before setting. And if there are significant amounts of surfactants in the formula, the manufacturing process sometimes requires a vacuum system to remove air bubbles.

Therefore, there is still a need for a water-based freshener system which does not require a flammable solubilizer or traditional amphiphilic surfactant yet has high diffusibility, low viscosity, and low foaming characteristics not associated with traditional amphiphilic surfactants.

SUMMARY OF THE INVENTION

Embodiments of the present invention are based on the unexpected discovery that certain glycol ethers, when used in sufficient quantity with respect to the fragrance-carrying immiscible oils and water, produce an air-freshener system that does not require flammable solubilizers, yet exhibits high diffusibility, low viscosity, and low foaming behavior, making it ideal for air fresheners that use wicks, pumps, or aerosol sprayers. More particularly, embodiments of the present invention comprise: (a) at least 40% water, preferably more than 50%, (b) 0.01% to 40% of a water-immiscible oil, preferably less than 25%, and (c) 10% to 50% of at least one glycol mono ether that contains from 1 to 3 ethylene glycol or propylene glycol units and a lipophilic chain having from 1 to 6 carbon atoms (percentages are expressed as weight of the component over the weight of the composition).

DETAILED DESCRIPTION OF THE INVENTION

Figure 1:
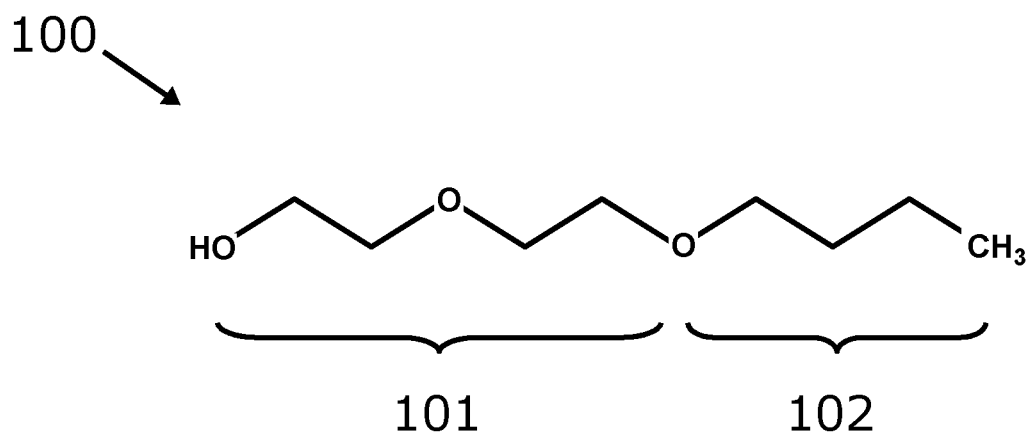
FIG. 1 shows the hydrophilic and lipophilic ends of diethylene glycol mono n-butyl ether.
Figure 2:
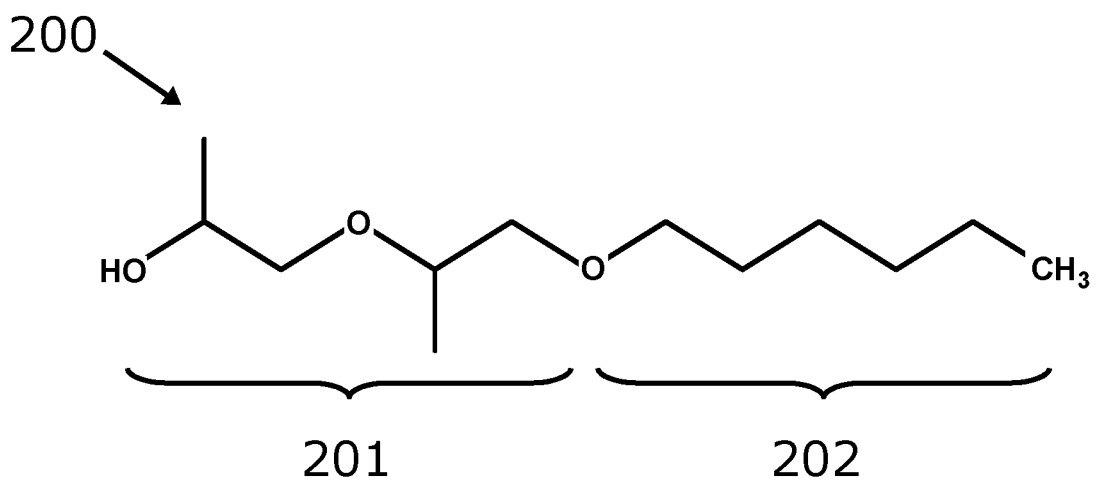
FIG. 2 shows the hydrophilic and lipophilic ends of dipropylene glycol mono n-hexyl ether.
Figure 3:
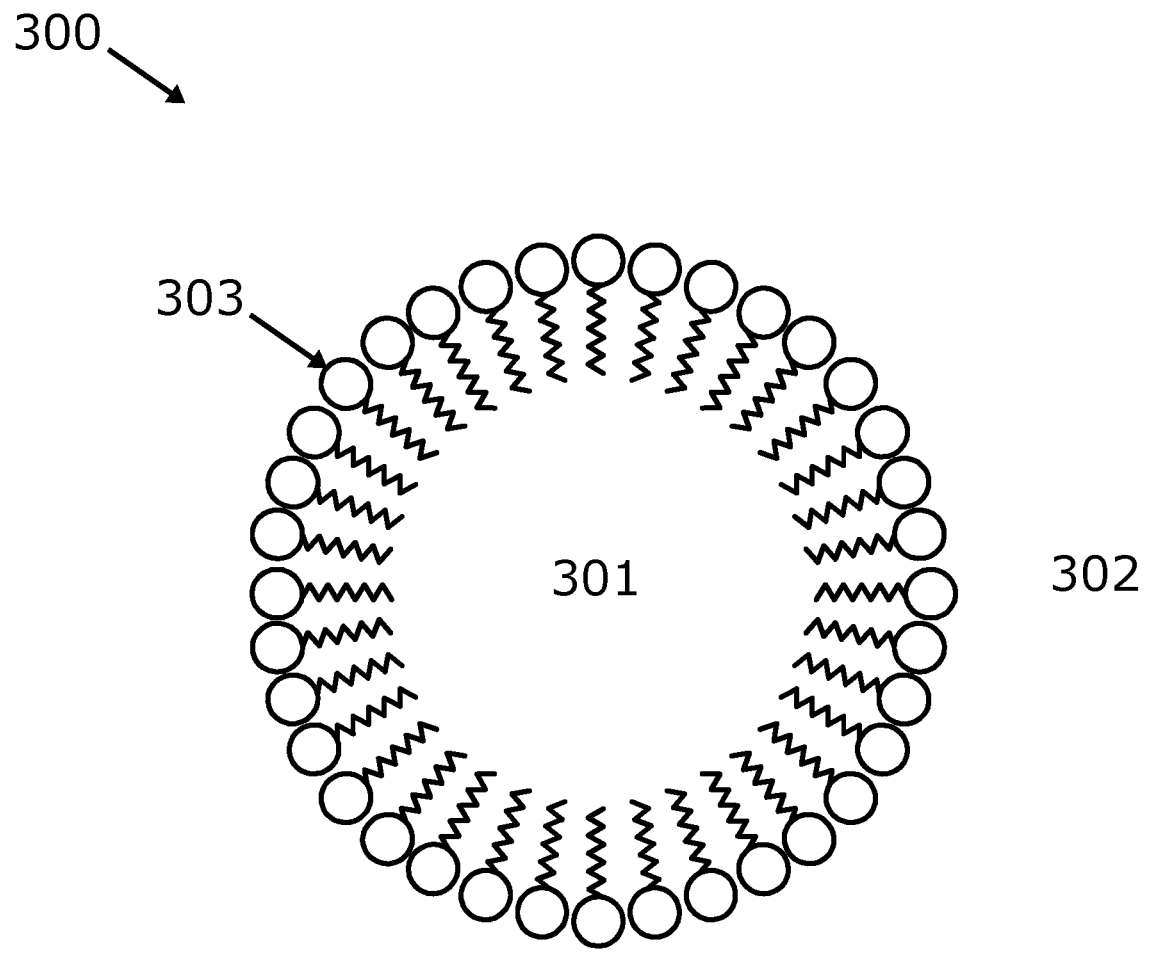
FIG. 3 shows an oil-in-water microemulsion in which a micelle is stabilized by an interfacial glycol ether.

It has been surprisingly found that a stable, optically clear microemulsion can be prepared by a glycol ether solvent without using any short chain alcohols or traditional amphiphilic surfactants. While glycol ethers have been used as co-solvents or solubilizing aids, glycol ethers have never been used as the only ingredients to solubilize water-immiscible oils. This unexpected discovery can be explained by the amphiphilic properties of glycol ethers. Glycol ethers comprises of two parts for each molecule. The poly-ol chain represents the hydrophilic part of the molecule. The linear or branched alkyl chain or phenyl group represents the lipophilic part of the molecule. For example, FIG. 1 shows a molecule of diethylene glycol mono n-butyl ether 100 having a lipophilic end 101 and a hydrophilic end 102. Similarly, FIG. 2 shows a molecule of dipropylene glycol mono n-hexyl ether 200 having a lipophilic end 201 and a hydrophilic end 202. FIG. 3 shows a swollen micelle 300 having an oil phase 301 inside micelle 300, a water phase 302 outside micelle 300, and an interfacial layer 303 that is composed of glycol ethers which stabilize micelle 300. Without this interfacial layer 303, oil droplets will coalesce and eventually separate out from the water phase. In a mixture comprising a plurality of micelle 300 structures, if each micelle 300 has a size of less than 100 nm, the whole mixture is a transparent microemulsion.

The hydrophilic-lipophilic balance (HLB) metric measures the hydrophilicity versus the lipophilicity of a surfactant according to equation 1:

$$HLB = 20 \times \frac{M_H}{M} \quad \text{(eq. 1)}$$

where $M_H$ is the molecular mass of the hydrophilic part of the molecule and M is the molecular mass of the whole molecule. An HLB value less than 10 generally means that the molecule will be more lipid-soluble/water-insoluble while an HLB value more than 10 generally means that the molecule will be more water-soluble/lipid-insoluble. Traditional surfactants used to solubilize fragrance oils typically have HLB values ranging from 12 to 16.

The inventors have found that certain glycol ethers may have similar HLB values, and as such, may be used to solubilize fragrance oils. The following lists a number of commercially-available glycol ethers and their calculated HLBs using equation 1:

| Chemical Nomenclature | Calculated HLB |
|---|---|
| ethylene glycol propyl ether | 11.7 |
| ethylene glycol n-butyl ether | 10.3 |
| ethylene glycol hexyl ether | 8.4 |
| ethylene glycol phenyl ether | 8.8 |
| diethylene glycol ethyl ether | 15.7 |
| diethylene glycol n-butyl ether | 13.0 |
| diethylene glycol hexyl ether | 11.1 |
| diethylene glycol phenyl ether | 11.5 |
| propylene glycol methyl ether | 16.7 |
| propylene glycol n-propyl ether | 12.7 |
| propylene glycol n-butyl ether | 11.4 |
| propylene glycol phenyl ether | 9.9 |
| dipropylene glycol methyl ether | 18.0 |
| dipropylene glycol n-propyl ether | 15.1 |
| dipropylene glycol n-butyl ether | 14.0 |
| dipropylene glycol phenyl ether | 12.7 |

In addition to having HLB values similar to those of traditional surfactants, certain glycol ethers have molecular structures that enhance their use as solubilizing agents. More preferably, mono-, di- or polyethylene glycol chains are linear structure and are easy to pack together in a microenvironment such as micelles. Less preferably, mono-, di- or polypropylene glycols have branched chains, making them more difficult to pack together in a microenvironment.

Further, in addition to having favorable HLB values and molecular structures, the size of the hydrophilic and lipophilic portions of the molecule play a role in the usefulness of glycol ethers as solubilizing agents. By way of example and not limitation, the hydrophilic part of the molecule may have 1 to 3 ethylene glycol or propylene units and the lipophilic part may be a linear or branched alkyl group with 1 to 6 carbons and may include a substituted or unsubstituted aromatic group.

Without limiting the solubilizing effect to a particular mechanism, the inventors believe that this combination of the balance of the hydrophilic to lipophilic portions, the shape of the molecule, and the size of the molecule gives certain glycol ethers solubilizing characteristics that are comparable to traditional surfactants agents without the unfavorable characteristics such as low diffusibility, high viscosity, and/or high foaming.

The inventors have identified the following glycol ethers as having the right combination of HLB, shape, and size to be suitable for use as solubilizing agents in fragrance systems: ethylene glycol propyl ether, ethylene glycol n-butyl ether, ethylene glycol hexyl ether, ethylene glycol phenyl ether, diethylene glycol ethyl ether, diethylene glycol n-propyl ether, diethylene glycol n-butyl ether, diethylene glycol n-pentyl ether, diethylene glycol hexyl ether, diethylene glycol phenyl ether, propylene glycol methyl ether, propylene glycol n-propyl ether, propylene glycol n-butyl ether, propylene glycol phenyl ether, dipropylene glycol methyl ether, dipropylene glycol n-propyl ether, dipropylene glycol n-butyl ether, dipropylene glycol phenyl ether, tripropylene glycol methyl ether and tripropylene glycol methyl ether. These glycol ethers are commercially available by Dow Chemicals under the names of Cellosolve™, Carbitol™ and Dowanol™. This list is exemplary only, and one of ordinary skill in the art could, without undue experimentation, find additional glycol ethers that are suitable for use in solubilizing fragrance oils.

The following exemplar compositions demonstrate embodiments of the present invention using various glycol ethers and fragrance oils, in combination with water and, in some cases, other ingredients common to fragrance systems.

Example 1 uses the fragrance BAC1342 formulated according to the following:

| Ingredients | CAS number | Percentage by weight |
|---|---|---|
| Ambroxan | 6790-58-5 | 0.0500 |
| Cedrol crystals | 77-53-2 | 0.6000 |
| Aldehyde C06 10% BB | MIXTURE | 0.1000 |
| Aldehyde C18 | 104-61-0 | 1.5000 |
| Allyl cyclohexyl propionate | 2705-87-5 | 1.0500 |
| Amber core | 139504-68-0 | 0.8000 |
| Benzylaldehyde | 100-52-7 | 0.0700 |
| Benzyl acetate | 140-11-4 | 2.4000 |
| Boisamrene forte | 58567-11-6 | 3.1000 |
| Cardamon W.I. Oil | 8000-66-6 | 0.0600 |
| Beta caryophellene | 87-44-5 | 0.8500 |
| Cashmeran | 33704-61-9 | 1.2500 |
| Cedramber | 19870-74-7 | 0.7500 |
| Cis jasmone | 488-10-8 | 0.0500 |
| Dihydro myrcenol | 18479-58-8 | 2.3500 |
| Ebanol | 67801-20-1 | 2.1600 |
| Ethyl linanool | 10339-55-6 | 6.2000 |
| Eugenol | 97-53-0 | 0.2100 |
| Floralozone | 67634-15-5 | 0.4000 |
| Gamma octalactone | 104-50-7 | 1.9300 |
| Gurjon balsam oil | 8030-55-5 | 0.2000 |
| Hedione | 24851-98-7 | 9.1500 |
| Hexyl cinnamic aldehyde | 101-86-0 | 4.3500 |
| Kephalis | 36306-87-3 | 0.7300 |
| Koumalactone 10% IN TEC | MIXTURE | 0.9700 |
| Methyl ionone gamma 70~ | 127-51-5 | 6.2000 |
| Methyl laitone 10% DPG | MIXTURE | 0.6800 |
| Methyl pample mousse | 67674-46-8 | 1.2100 |
| Styrallyl acetate | 93-92-5 | 0.1800 |
| Timbersilk | 54464-57-2 | 9.6500 |
| DPG—Dipropylene glycol | 110-98-5 | 40.8000 |

To demonstrate the efficacy of the use of glycol ethers as the solubilizing agent for the freshener oil, three freshener compositions were prepared using BAC1342 at 20% by weight. Two of the compositions used traditional used surfactants (polysorbate 20 and octylphenol oxylate), and the third used a glycol ether (diethylene glycol mono butyl ether). The appearances of the compositions were recorded and their viscosities were measured using a Brookfield Rotational Viscometer with Spindle #1 and Rotational Speed at 12 RPM:

| Air Freshener Compositions | | | Viscosity |
|---|---|---|---|
| Ingredients | % by weight | Appearance | (cps) |
| Sample # 1 | | | |
| BAC1342 | 20 | transparent, macroscopically one phase | 10.0 |
| Diethylene glycol mono butyl ether* | 35 | | |
| Distilled water | 45 | | |
| Sample # 2 | | | |
| BAC1342 | 20 | translucent, separated into two phases | 169.0 |
| Polysorbate 20** | 35 | | |
| Distilled water | 45 | | |
| Sample # 3 | | | |
| BAC1342 | 20 | cloudy | 186.0 |
| Octylphenol ethyoxylate*** | 35 | | |
| Distilled water | 45 | | |

*Commercially available as Butyl Carbitol from Dow Chemical Company
**Commercially available as Tween 20 from Croda
***Commercially available as Triton X-100 from Dow Both of the prior art surfactants fail to form transparent microemulsion with 20% BAC1342 in distilled water. Additionally, both compositions demonstrate high viscosities preventing their applications in air freshener formats such as room sprays. Unexpectedly, the diethylene glycol mono butyl ether forms clear microemulsion with such high level of fragrance oil without any other surfactants. The viscosity is low enough to be applied in various formats such as room sprays and plug-ins.

Example 2 combines the following:

| Ingredients | Percentage by weight |
|---|---|
| Hydroxycitronellol | 25 |
| Diethylene glycol mono butyl ether | 25 |
| Distilled water | 50 |

Hydroxycitronellol has a clogP of 1.55 and its water solubility is 393 mg/L at 25° C. The procedure to prepare the clear microemulsion is independent on the order of addition. In this case, diethylene glycol mono butyl ether is premixed with distilled water. Then hydroxycitronellol is added. The formation of microemulsion seems spontaneous. Using a shaker or rocker, the mixture turns perfectly clear after 5-30 minutes of agitation.

Example 3 combines the following:

| Ingredients | Percentage by weight |
|---|---|
| Methyl dihydrojasmonate* | 15 |
| Diethylene glycol mono butyl ether | 35 |
| Distilled water | 50 |

*Commercially available as Hedione ® from Firmenich

Methyl dihydrojasmonate is a widely used fragrance ingredient. It has a clogP of 2.65 and its water solubility is 91.7 mg/L at 25° C. Methyl dihydrojasmonate is premixed with diethylene glycol mono butyl ether, followed by addition of distilled water. The mixture turns perfectly clear after 5-30 minutes of agitation.

Example 4 combines the following:

| Ingredients | Percentage by weight |
|---|---|
| 3-(4-tert-butylphenyl)butanal* | 10 |
| Diethylene glycol mono butyl ether | 40 |
| Distilled water | 50 |

*Commercially available as Lilial ® from IFF 3-(4-tert-butylphenyl)butanal has a clogP of 4.22 and its water solubility is 38 mg/L at 25° C. 3-(4-tert-butylphenyl) butanal is premixed with diethylene glycol mono butyl ether, followed by addition of distilled water. The mixture turns perfectly clear after 5-30 minutes of agitation.

Example 5 combines the following:

| Ingredients | Percentage by weight |
|---|---|
| Beta-caryophyllene | 2 |
| Diethylene glycol mono butyl ether | 49 |
| Distilled water | 49 |

Beta-caryophyllene is among the mostly hydrophobic fragrance ingredients. It is composed entirely of hydrocarbons and has a clogP of 6.3. It has no functional groups to form hydrogen bonds with water molecules. Its water solubility is merely 0.05 mg/L at 25° C. The beta-caryophyllene is premixed with diethylene glycol mono butyl ether, followed by addition of distilled water. The mixture turns perfectly clear after 5-30 minutes of agitation.

Example 6 combines the following:

| Ingredients | Percentage by weight |
|---|---|
| BAC1342 | 20 |
| Diethylene glycol mono butyl ether | 35 |
| Imidazolidinyl urea* | 0.3 |
| Distilled water | 44.7 |

*Commercially available as Iscarguard DU from ISCA

BAC1342 is premixed with the diethylene glycol mono butyl ether, the imidazolidinyl urea is added to distilled water, and the oil phase and the water phase are mixed. The mixture turns perfectly clear after 5-30 minutes of agitation, and the imidazolidinyl urea acts as a preservative to control microbial growth.

Example 7 combines the following:

| Ingredients | Percentage by weight |
|---|---|
| BAC1342 | 20 |
| Diethylene glycol mono butyl ether | 35 |
| Imidazolidinyl urea | 0.3 |
| Yellow water-soluble dye | 0.1 |
| Distilled water | 44.6 |

The imidazolidinyl urea and the yellow dye are added to distilled water and mixed well, the BAC1342 is added to the diethylene glycol mono butyl ether, and the oil phase and the water phase are mixed. The mixture turns perfectly clear after 5-30 minutes of agitation, and the imidazolidinyl urea and the yellow dye provide microbial control and color respectively.

Example 8 combines the following:

| Ingredients | Percentage by weight |
|---|---|
| BAC1342 | 20 |
| Diethylene glycol mono butyl ether | 35 |
| Imidazolidinyl urea | 0.3 |
| Yellow water-soluble dye | 0.1 |
| Rose essential water* | 44.6 |

*Commercially available from Carrubba Inc.

The imidazolidinyl urea and the yellow dye are added to the Rose Essential Water and mixed well, the BAC1342 is added to the diethylene glycol mono butyl ether, and the oil phase and the water phase are mixed. The mixture turns perfectly clear after 5-30 minutes of agitation.

The foregoing embodiments provide a sampling of embodiments of the present invention. Based on the present disclosure, one of ordinary skill in the art could readily develop other fragrance systems by substituting glycol ethers, modifying the percentages of the components, adding or substituting other dyes, microbial control agents, and other ingredients typically found in fragrance systems, and so on, provided that such fragrance systems are free of (or substantially free of) alcohols or other volatile materials and have high diffusibility, low viscosity, and low foaming characteristics.

The invention claimed is:

1. An air freshener system consisting of:
   water in a portion by weight of between 40% and 60%;
   water-immiscible oil in a portion by weight of between 0.01% and 40%; and
   glycol ether in a portion by weight of between 10% and 70%,
   where the glycol ether has a lipophilic aliphatic chain comprising between 1 to 6 carbons and a hydrophilic chain comprising between 1 and 3 glycol units.

2. The system of system of claim 1, where:
   the glycol units are ethylene glycol units.

3. The system of system of claim 1, where:
   the glycol units are propylene glycol units.

4. The system of system of claim 1, where:
   the glycol ether is diethylene glycol mono butyl ether.

5. The system of system of claim 1, where:
   the glycol ether comprises a phenyl ring.

6. The system of system of claim 1, where:
   the glycol ether comprises a polyaromatic ring.

7. The system of claim 1, where:
   the water-immiscible oil is present in a portion by weight of between 0.01% and 20%.

8. The system of claim 1, Where:
   the water is present in a portion by weight of between 50% and 50%.

9. The system of claim 1, where:
   the water comprises at least one of tap water, deionized water, and distilled water.

10. The system of claim 1, where:
    the glycol ether has a calculated HLB value between 12 and 16.

11. An air freshener base consisting of:
    water in a portion by weight of between 40% and 60%;
    glycol ether in a portion by weight of between 40% and 60%; and
    a preservative in a portion by weight of between 0.1% and 2.0%,
    where the glycol ether has a lipophilic aliphatic chain comprising between 1 to 6 carbons and a hydrophilic chain comprising between 1 and 3 glycol units.

12. The air freshener base of claim 1, where:
    the glycol ether is diethylene glycol mono butyl ether.

13. The air freshener base of claim 1, where:
    the glycol ether is dipropylene glycol mono n-hexyl ether.

14. An air freshener system consisting of:
    water in a portion by weight of between 40% and 60%;
    water-immiscible oil in a portion by weight ot between 0.01% and 40%; and
    glycol ether in a portion by weight of between 10% and 70%,
    where the glycol ether has hydrophilic-lipophilic balance between 12 and 16.

15. The system of system of claim 14, where:
    the glycol ether is diethylene glycol mono butyl ether.

16. The system of system of claim 14, where:
    the glycol ether is dipropylene glycol mono n-hexyl ether.

* * * * *